United States Patent [19]
Ikeda et al.

[11] Patent Number: 5,929,299
[45] Date of Patent: Jul. 27, 1999

[54] HELICOBACTER PYLORI-COLONIZED MONGOLIAN GERBILS, METHOD FOR PREPARATION THEREOF, AND METHOD FOR SCREENING ANTI-HELICOBACTER PYLORI SUBSTANCE USING THEM

[75] Inventors: Yoshifumi Ikeda; Fumihiro Hirayama; Shiro Takagi, all of Fukuoka, Japan

[73] Assignee: Yoshitomi Pharmaceutical Industries, Ltd., Osaka, Japan

[21] Appl. No.: 08/693,100

[22] PCT Filed: Dec. 8, 1995

[86] PCT No.: PCT/JP95/02531

§ 371 Date: Aug. 9, 1996

§ 102(e) Date: Aug. 9, 1996

[87] PCT Pub. No.: WO96/18291

PCT Pub. Date: Jun. 20, 1996

[30] Foreign Application Priority Data

Dec. 13, 1994 [JP] Japan ................................ 6-308618

[51] Int. Cl.$^6$ ............................ C12N 5/00; C12N 15/00; C12N 1/00
[52] U.S. Cl. ................................... 800/9; 800/3; 435/243
[58] Field of Search .................. 800/2, DIG. 5, 800/4, 8, 9; 424/9.1, 9.2; 435/4, 243, 248, 253.6

[56] References Cited

U.S. PATENT DOCUMENTS 5,625,124  4/1997  Falk et al. .................................. 800/2

OTHER PUBLICATIONS

Catalogue of Bacteria & Bacteriophages, 17th edition, 1989, American Type Culture Collection, Rockville, MD, p. iv.
Yokota et al., "Colonization of *Helicobacter pylori* in the Gastric Mucosa of Mongolian Gerbils", Microbiol. Immunol., vol. 35 (6), pp. 475–480, 1991.
Shuto et al., "Experimental Gastritis Induced by *Helicobacter pylori* in Japanese Monkeys", Infection and Immunity, vol. 61, No. 3, pp. 933–939, Mar. 1993.
Euler et al., "Evaluation of Two Monkey Species (*Macaca mulatta* and *Macaca fascicularis*) as Possible Models for Human *Helicobacter pylori* Disease", Journal of Clinical Microbiology, vol. 28, No. 10, pp. 2285–2290, Oct. 1990.
Engstrand et al., "Inoculation of Barrier–Born Pigs with *Helicobacter pylori:* a Useful Animal Model for Gastritis Type B", Infection and Immunity, vol. 58, No. 6, pp. 1763–1768, Jun. 1990.
Dick–Hegedus et al., "Use of a Mouse Model to Examine Anti–*Helicobacter pylori* Agents", Scand. J. Gastroenterol, vol. 26, pp. 909–915, 1991.
Xia et al., "Enhanced Cultivation of *Helicobacter pylori* in Liquid Media", J. Clin. Pathol., vol. 46, pp. 750–753, 1993.
Cellini et al., "New Plate Medium for Growth and Detection of Urease Activity of *Helicobacter pylori*", Journal of Clinical Microbiology, vol. 30, No. 5, pp. 1351–1353, May 1992.
Mirza et al., "*Helicobacter pylori:* Isolation from Gastric Biopsy Specimens", Annals of Tropical Medicine and Parasitology, vol. 87, No. 5, pp. 483–486, 1993.

*Primary Examiner*—Deborah Crouch
*Assistant Examiner*—Michael C. Wilson
*Attorney, Agent, or Firm*—Wenderoth, Lind & Ponack, L.L.P.

[57] ABSTRACT

*Helicobacter pylori*-colonized Mongolian gerbils prepared by oral inoculation of a broth culture obtained from a liquid culture of *Helicobacter pylori,* to the Mongolian gerbils for intragastric colonization of *Helicobacter pylori.* These Mongolian gerbil models are useful for screening the therapeutic efficacies of drugs against *Helicobacter pylori,* as well as elucidation of pathology of *Helicobacter pylori* disease in humans. Moreover, the medium of the present invention for isolating *Helicobacter pylori,* which is supplemented with vancomycin, trimethoprim, amphotericin B, polymyxin B and 2,3,5-triphenyltetrazolium chloride, enables selective and efficient detection of *Helicobacter pylori* colonized in their Mongolian gerbils which have microorganisms living in stomach. A combined use of the above-mentioned Mongolian gerbil models and the medium for isolating *Helicobacter pylori* enables screening of an anti-*Helicobacter pylori* substance at an animal levels thereby enabling accurate prediction of clinical effects of the anti-*Helicobacter pylori* substance.

3 Claims, No Drawings

HELICOBACTER PYLORI-COLONIZED MONGOLIAN GERBILS, METHOD FOR PREPARATION THEREOF, AND METHOD FOR SCREENING ANTI-HELICOBACTER PYLORI SUBSTANCE USING THEM

BACKGROUND OF THE INVENTION

The present invention relates to Helicobacter pylori-colonized Mongolian gerbils usable for (1) screening the therapeutic effect of a drug for Helicobacter pylori which is considered to be the pathogen of gastric ulcer and duodenal ulcer, recurrence thereof, and diseases such as gastric carcinoma, or (2) for the elucidation of pathology in the above-mentioned diseases caused by infection with Helicobacter pylori, and to a method for preparation thereof. The present invention also relates to a medium for isolation of Helicobacter pylori, and further to a method for screening an anti-Helicobacter pylori substances comprising the use thereof.

DESCRIPTION OF THE RELATED ART

Helicobacter pylori (hereinafter sometimes referred to as H. pylori) is a Gram negative bacterium isolated from gastric mucosa of patients with active chronic gastritis (Warren, J. R. & Marshall, B. J. Lancet i: 1273–1275, 1983). H. pylori is a 0.5 $\mu$m wide, 3–5 $\mu$m long Gram negative spirally curved rod having several polar flagella and flagella sheaths at one or both ends of the cell. H. pylori grows in a microaerophilic environment, cannot grow under aerobic conditions and grows poorly under the anaerobic conditions. It grows at 37° C. and scarcely grows at a temperature lower than 25° C. and higher than 42° C. The bacterium is notably characterized in that it evidently produces urease (Mobley, H. L. et al., Clin. Microbiol., 26, 831–8369 1988).

H. pylori is present in the mucous layer in the gastric mucosal epithelium of humans and swims in the viscous mucous layer using the characteristic flagella. H. pylori specifically resides in the surface layer of the epithelium cells and the crevice therein, which provide the most comfortable living environment where gastric acidity is neutral, and lives by utilizing hemin, urea and so on (Hazell, S. L., Adrian, L., J. Infect. Dis., 153, 658–663, 1986).

As to the pathogenesis of the diseases caused by H. pylori, mucous membrane disorder concept (Hazell, S. L., Adrian, L., J. Infect. Dis., 153, 658–663, 1986), leaking roof concept (Goodwin C. S., Lancet ii, 1467–1469, 1988) and gastrin link concept (Levi, S. et al., Lancet i, 1167–1168, 1989) have been proposed.

The mucous membrane disorder caused by H. pylori is mostly ascribed to its strong urease activity (Hazell, S. L., Adrian, L., J. Infects Dis., 153, 658–663, 1986). The urea present in the gastric juice is decomposed by the urease of H. pylori and converted to a large amount of ammonium and carbon dioxide. The ammonium concentration in the gastric juice is significantly high in the H. pylori positive groups and histological epitheliocyte disorder and an increased ulcer coefficient have also been reported in the experiments where ammonium was orally administered to rats (Murakami, M. et al., Clin. Gastroenterol. 12 (Suppl. 1), S104–109, 1990).

Also, there is a report on reduced amounts of PAS (periodic acid schiff)-positive mucosal juice in the gastric mucosa of patients who tested positive to H. pylori suggesting possible degradation of a gastric mucosa-protective activity due to the decomposition of mucosal juice by the protease of H. pylori (Nakajima, ,M et al., Drug Investigation, (Suppl. 1), 60, 1990). It has been further reported that leukotriene B4 activity is high in the gastric mucosa where striking infiltration of leukocytes by H. pylori is observed (Uchida, T. et al., Therapeutic Research, 12, 85–90, 1991) and that the mucous membrane disorder is caused by the action of phospholipase A2 on bile acid which flows reversely into the stomach.

In 1988, Leunk et al. reported the presence of a cytovacuolating toxin in the supernatant of H. pylori culture. The toxin was isolated and purified by Cover et al (Cover, T. L. & Blaser, M. J., J. Biol. Chem. 267, 10570–10575, 1992). Reports on the toxin have documented that it delays cure of ulcer by hindering the rotation of cells near the ulcer (Chang, K. et al., Gastroenterology, 104 (Suppl), A52, 1993) and that it acts synergistically with ammonium on cytovacuolation (Sommi, F. et al., Gastroenterology, 104 (Suppl.), A196, 1993).

In recent years, a disorder of gastric mucosa, which is caused by (1) acetoaldehyde produced in the stomach by the alcohol dehydrogenase activity possessed by H. pylori (Salmela, K. S. et al., Gastroenterology, 105, 325–330, 1990), (2) monochloramine produced in the presence of ammonium (Saida, H. et al., Nihon Shokakibyo Gakkai Zasshi 90, 1949, 1993), and (3) interleukin 8 (Crowe, S. E. et al., Gastroenterology, 104, A687, 1993) have been drawing attention.

With regard to the relationship between peptic ulcer and H. pylori, the involvement of H. pylori has been strongly suggested in view of the very high isolation frequency of H. pylori, particularly in duodenal ulcer, and infection with H. pylori is considered to be responsible for a prolonged cure and recurrence of peptic ulcer (see, for example, Raws EAJ, et al., Gastroenterology, 94, 33–40, 1988).

With regard to the relationship between gastritis and H. pylori, the causality has been suggested based on oral infection tests in humans (Morris, A. & Nicholoson, G. Am., J. Gastroenterology, 82, 192–199, 1987, Marshall, B. J. et al., Med. J. Aust., 142, 436–439, 1985).

The isolation frequency of H. pylori in gastritis is high and the correlation has been confirmed between the cell counts of H. pylori, and the increase in neutrophil, which is an index of activeness of gastritis, and the level of clinical symptoms with accompanying infiltration of lymphocytes. Moreover, the development of gastritis in antrum of stomach with flare and erosion was endoscopically observed in animal tests using Japanese monkeys (Shuto, R. et al., Infect. Immun., 619 933–939, 1993).

The number of reports on the progression to stomach cancer, which is caused by persistent H. pylori infection via atrophic gastritis and intestinal metaplasia, is recently on the rise. In 1991, Parsonnet et al. determined the IgG antibody titer of anti-H. pylori using a serum preserved for about 25 years and found a strong correlation between occurrence of stomach cancer and patients having the antibody. It has been also founds by epidemiological studies, that morbidity of and percentage of deaths from stomach cancer are high in the region where H. pylori antibody positive ratio is high (Parsonnet, J. et al. N. Engl. J. Med., 325, 1127–1131, 1991).

Accordingly, there has been a strong demand in recent years for the development of a drug effective for the eradication of Helicobacter pylori. Heretofore, however, an efficient screening system has not yet been established. To be specific, although the antibacterial activity can be determined with ease in vitro, the data do not indicate accurate activity thereof in vivo, which in turn makes accurate prediction of clinical effects difficulty, and impairs reliability of the prediction.

It is also critical to establish an animal infection model for the elucidation of pathology of long-term infection with *Helicobacter pylori*. The infection models known to date which have reportedly been susceptible to *Helicobacter pylori* infection include gnotobiotic pig, gnotobiotic beagle, cynomolg monkey, Rhesus monkey, Japanese monkey, nude mouse and the like, which are not satisfactory in terms of reproducibility and histopathological changes.

In this connection, Yokota et al. reported that they suspended colonies of *Helicobacter pylori* cultured on an agar plate in a phosphate buffer, added carboxymethylcellulose and urea to the suspension, orally administered to Mongolian gerbils, inclusive of those administered with indomethacin by subcutaneous route, and removed gastric mucosa to examine colonization rate of *Helicobacter pylori* by urease testing and immunological staining (Yokota, K. et al Microbiol. Immunol., 35(6):475–480, 1991). According to this report, the colonization rate of *Helicobacter pylori* was 44–72% in Mongolian gerbils without pre-treatment and 77–86% in the group pre-treated with indomethacin, and the results are not satisfactory. Furthermore, inflammatory response induced by *Helicobacter pylori* was mild, and they are not suitable as experimental models.

SUMMARY OF THE INVENTION

The present invention aims at providing *Helicobacter pylori*-colonized Mongolian gerbils usable for (1) screening the therapeutic effect of a drug for *Helicobacter pylori* which is considered to be the pathogen of gastric ulcer and duodenal ulcer, recurrence thereof and diseases such as gastric carcinoma, or (2) for the elucidation of the pathology in the above-mentioned diseases caused by infection with *Helicobacter pylori*, and a method for preparation thereof The present invention also aims at providing a medium for selective isolation of *Helicobacter pylori*, and further a method for screening an anti-*Helicobacter pylori* substance, comprising the use of the *Helicobacter pylori*-colonized Mongolian gerbils and the medium for selectively isolating *Helicobacter pylori*.

DESCRIPTION OF THE PREFERRED EMBODIMENTS

The present inventors have conducted intensive studies for the purpose of achieving the above-mentioned objects, and found that direct oral administration of a culture broth of *Helicobacter pylori*, to Mongolian gerbils (*Meriones unguiculatus*) leads to successful preparation of Mongolian gerbils infection models exhibiting nearly 100% colonization rate of *Helicobacter pylori* into gastric mucosa, and that the use of a medium containing specific antibacterial substances enables selective isolation of *Helicobacter pylori*, which resulted in the-completion of the present invention.

Accordingly, the present invention relates to (1) *Helicobacter pylori*-colonized Mongolian gerbils obtained by oral inoculation of a broth culture of *Helicobacter pylori* which is obtained by liquid culture of *Helicobacter pylori*, to Mongolian gerbils for intragastric colonization of *Helicobacter pylori*, (2) a method for preparing the *Helicobacter pylori*-colonized Mongolian gerbils, comprising orally inoculating a broth culture obtained by liquid culture of *Helicobacter pylori*, to Mongolian gerbils for intragastric colonization of *Helicobacter pylori*, (3) a medium for isolating *Helicobacter pylori*, which comprises vancomycin, trimethoprim, amphotericin B, polymyxin B and 2,3,5-triphenyltetrazolium chloride, and (4) a method for screening an anti-*Helicobacter pylori* substance, comprising a combined use of a medium for isolating *Helicobacter pylori*, which comprises vancomycin, trimethoprim, amphotericin B, polymyxin B and 2,3,5-triphenyltetrazolium chloride, and *Helicobacter pylori*-colonized Mongolian gerbils prepared by oral administration of a broth culture obtained by liquid culture of *Helicobacter pylori*, to the Mongolian gerbils for intragastric colonization of *Helicobacter pylori*.

The *Helicobacter pylori* to be used in the present invention is exemplified by *Helicobacter pylori* ATCC 43504 (also available as *Helicobacter pylori* NCTC 13637) and *Helicobacter pylori* ATCC 43526 (also available as *Helicobacter pylori* NCTC 11916). These may be mutated by a conventional method or clinical isolates thereof may be used. The *Helicobacter pylori* to be used in the present invention is preferably freeze-preserved as a seed culture which is obtained by inoculation of *Helicobacter pylori* to brucella liquid medium supplemented with inactivated horse serum and subsequent shake culture under microaerobic conditions for 24 hours. This seed culture is inoculated to brucella broth medium supplemented with inactivated horse serum and shake-cultured under microaerobic conditions for 24 hours to give a fresh culture broth.

The Mongolian gerbil models of the present invention with intragastrically colonized *Helicobacter pylori* are prepared by orally inoculating, with an oral probe, a fresh culture of *Helicobacter pylori* obtained as above, to the Mongolian gerbils that have been fasted for 16–24 hours prior to inoculation, and fasting and depriving water for more than 3 hours after the inoculation. The Mongolian gerbils to be used are of the strain (inbred strain, distributed from 1977) known as MGS/Sea described in Okumura et al. (Exp. Anim. 43(5), 719–723, 1995), with more preference given to gnotobiotic Mongolian gerbils which require no pre-treatments with, for example, indomethacin.

The intragastric colonization of *Helicobacter pylori* in Mongolian gerbils is confirmed as follows. That is, the stomachs of *Helicobacter pylori*-infected Mongolian gerbils prepared as above are aseptically excised, placed in phosphate buffer—physiological saline after removing their contents, and homogenized with a homogenizer and the like. The supernatant is appropriately diluted, and a suitable amount thereof is inoculated, for example, onto a medium for isolating *Helicobacter pylori* which is provided by the present invention. The medium is cultured under microaerobic conditions at about 37° C. and the characteristic colonies (e.g., dark brown swelling colony) of *Helicobacter pylori* are counted. By counting the viable cells, the colonization ratio of *Helicobacter pylori* can be determined easily. The Mongolian gerbils of the present invention achieve nearly 100% colonization ratio. As mentioned later, the Mongolian gerbil models of the present invention can be used for screening an anti-*Helicobacter pylori* substance, as well as for the elucidation of the pathology associated with *Helicobacter pylori* infections in humans.

The medium for isolating *Helicobacter pylori* of the present invention contains vancomycin, trimethoprim, amphotericin B, polymyxin B and 2,3,5-triphenyltetrazolium chloride. The content of each ingredient is 2–30 mg for vancomycin, 1–5 mg for trimethoprim, 1–10 mg for amphotericin B, 1,000–3,000 international unit (IU) for polymyxin-B and 10–100 mg for 2,3,5-triphenyltetrazolium chloride, respectively per one liter of the medium base.

The medium base is preferably GC medium (manufactured by Difco), brucella medium (manufactured by BBL) or BHI (Brain heart infusion) agar medium (manufactured by Difco), which is used after supplementing with 5–10% defibrinated horse blood. A particularly preferable medium composition for the selective isolation of *Helicobacter pylori* is GC medium supplemented with 5% defibrinated horse blood, which is further added with vancomycin 10 mg/l, trimethoprim 5 mg/l, amphotericin B 2 mg/l polymyxin B 2,500 IU/l and 2,3,5-triphenyltetrazolium chloride 50 mg/l (hereinafter this medium is sometimes referred to as HPSMY medium).

The method for screening an anti-*Helicobacter pylori* substance of the present invention comprises a combined use of the above-mentioned Mongolian gerbils with intragastrically-colonized *Helicobacter pylori,* and medium for isolating *Helicobacter pylori.* That is, *Helicobacter pylori* is inoculated into the stomach of Mongolian gerbils and a test compound is orally or parenterally administered 1–3 times a day for 5–14 days during the period when histopathological changes by bacterial colonization become evident (4–6 weeks after inoculation). At a predetermined time after the completion of the administration, the stomach is excised. The homogenate supernatant is diluted appropriately and a 0.1 ml aliquot is inoculated onto the medium (e.g., HPSMY medium) of the present invention for isolating *Helicobacter pylori,* and the medium is cultured under microaerobic conditions at about 37° C. for 3–7 days. The colonies of *Helicobacter pylori* which emerged after culture are counted. The viable cell counts of the stomach of Mongolian gerbils are calculated from the colony counts and the dilution ratio of the supernatant.

The viable cell counts of the stomach of Mongolian gerbils without administration of the drug are also calculated in the same manner. Comparison of the viable counts of the drug-administered group and non-administered group reveals the eradication effect of *Helicobacter pylori* by the drug.

The present invention is described in more detail by referring to Examples and Experimental Examples to which the present invention is not limited.

EXAMPLE 1

Using a 500 ml flask with baffles, *Helicobacter pylori* ATCC 43504 is inoculated into brucella broth medium (100 ml, manufactured by BBL) supplemented with 10% inactivated horse serum, and incubated by shake culture in a $CO_2$ incubator (8% $CO_2$, 37° C.) for about 24 hours (rotation speed: 140 rpm). This culture is divided in small portions and freeze-preserved as a seed culture in a freezer at –80° C.

This seed culture is naturally thawed at room temperature and inoculated into brucella broth medium (100 ml) in a 500 ml flask with baffles, which has been supplemented with 10% inactivated horse serum, to a concentration of 3%. The medium is subjected to shake culture in a $CO_2$ incubator for about 20 hours (rotation speed: 140 rpm). The culture (0.5 ml, cell count:about $2 \times 10^8$ cells/ml) obtained by shake culture as above is inoculated, using an oral probe, to male Mongolian gerbils (MGS/Sea, 7 weeks old, body weight 45–55 g, 5 per group, Seiwa Experimental Animals Ltd.) fasted for about 20 hours. The animals are bred in a fasting cage for about 4 hours after the inoculation without giving drinking water.

EXAMPLE 2

Vancomycin (10 mg/l, Sigma), trimethoprim (5 mg/l, Sigma), amphotericin B (2 mg/l, Sigma), polymyxin B (2,500 IU/l, Sigma) and 2,3,5-triphenyltetramolium chloride (50 mg/l, Wako Pure Chemicals) were added to GC medium supplemented with 5% defibrinated horse blood to prepare HPSMY medium.

EXAMPLE 3

*Helicobacter pylori* seed culture under freeze-preservation is naturally thawed at room temperature and inoculated into brucella broth medium (100 ml) in a 500 ml flask with baffles, which has been supplemented with 10% inactivated horse serum, to a concentration of 3%. The medium is subjected to shake culture in a $CO_2$ incubator for about 20 hours.

The culture is inoculated to male Mongolian gerbils (MGS/Sea, 7 weeks old, body weight 45–55 g, 5 per group, Seiwa Experimental Animals Ltd.) fasted for about 20 hours in a dose of 0.5 ml per animal. The animals are bred in a fasting cage for about 4 hours after the inoculation without giving drinking water. At 4 weeks postinoculation, an antibiotic, amoxicillin (1 or 3 mg/kg), is orally inoculated twice a day for 5 days.

At 4 weeks after the final administration of the drugs the stomachs are aseptically excised, placed in phosphate buffer-physiological saline (10 ml) after softly removing their contents, and homogenized with a glass homogenizer. The supernatant is appropriately diluted and an aliquot (0.1 ml) thereof is inoculated onto the isolation medium of Example 2. The medium is cultured for 5 or 6 days in a $CO_2$ incubator and dark brown swelling colonies characteristic of *Helicobacter pylori* are counted.

The viable counts of *Helicobacter pylori* per animal of Mongolian gerbils are calculated from viable counts and dilution ratio of respective dilutions, and expressed in log CFU/stomach. The viable counts in the stomach are determined in completely the same manner with respect to the group without administration of the antibiotic. The difference between the viable counts of the group administered with the antibiotic and the group without the administration is statistically analyzed by Tukey's method for detection of significant difference.

EXPERIMENTAL EXAMPLE 1

The stomachs of the *Helicobacter pylori*-infected Mongolian gerbils prepared in Example 1 are aseptically excised, placed in phosphate buffer—physiological saline (10 ml) after softly removing their contents, and homogenized with a glass homogenizer. The supernatant is appropriately diluted and an aliquot (0.1 ml) thereof is inoculated onto a medium for isolating *Helicobacter pylori.* The medium is cultured for about 5–6 days in a $CO_2$ incubator, and dark brown swelling colonies characteristic of *Helicobacter pylori* are counted. The viable counts (CFU:colony forming unit) in the stomach of the models of Example 1 was kept at the $10^4$–$10^5$ level from one month to 12 months postinfection.

The excised stomach was fixed in a 10% neutral buffered formalin. The corpus and antrum of the stomach were sectioned, embedded in paraffin, and stained with hematoxylin-eosin (HE), after which they were subjected to microscopic histopathological examination. The histopathological evaluation of gastritis followed the method of Raus et al (Gastroenterology 94:33–40, 1988) using gastritis scores.

As a result, histological changes with accompanying inflammatory infiltration of cells, mainly neutrophils, were observed at lamina propria of antrum from 2 weeks postinfection, and emergence of lympho follicles in lamina propria of antrum and gastric submucosa, as well as evident superficial epithelial erosion were observed 6 weeks later, At 6 weeks postinfection, the gastritis score in all five Mongolian gerbils reached 8. Inflammatory changes were reinforced with passage of time, and the titer of IgG antibody to *Helicobacter pylori* increased with passage of time. In the observation up to 12 months postinfection, one or two typical gastric ulcer emerged on the border of corpus and antrum from about 6 months, and 7 of 10 cases under observation up to 12 month developed gastric ulcer. In addition, intestinal metaplasia was observed around the ulcer. The gastric ulcer thus developed closely resembled that in humans in terms of location, pathohistologic images and so on.

EXPERIMENTAL EXAMPLE 2

*Helicobacter pylori* (*H. pylori*) ATCC 43504 was cultured in GC medium supplemented with 5% defibrinated horse blood under microaerobic conditions at about 37° C. for 3 days. The colonies grown were harvested and suspended in 1 ml of phosphate buffer to give a bacterial solution, Other test bacteria (*Staphylococcus aureus, Enterococcus faecalis, Bacillus subtilis, Candida albicans*) were subjected to stationary culture in BHI broth medium (manufactured by Difco) at 37° C. for about 16 hours to give bacterial solutions.

These bacterial solutions were diluted appropriately and aliquots (0.1 ml) thereof were spread on HPSMY medium or GC medium. The media were incubated under microaerobic conditions at 37° C. for 4–6 days and colonies grown were counted. The results of three repeats of these procedures are shown in the following in mean±SE of viable counts (log CFU/ml). The HPSMY medium did not affect growth of *H. pylori* but selectively inhibited growth of other bacteria and fungi.

| Test bacteria | Viable counts (log CFU/ml) | |
|---|---|---|
| | GC medium | HPSMY medium |
| i H. pylori ATCC 43504 | 9.00 ± 0.08 | 8.61 ± 0.12 |
| S. aureus FDA 209P | 8.51 ± 0.03 | <1 |
| E. faecais LS-101 | 8.10 ± 0.02 | <1 |
| B. subtilis ATCC 6633 | 7.33 ± 0.02 | <1 |
| C. albicans IFO 1060 | 7.10 ± 0.02 | <1 |

EXPERIMENTAL EXAMPLE 3

The colonies of *Helicobacter pylori* ATCC 43504 grown by culture in GC medium supplemented with 5% defibrinated horse blood under microaerobic conditions at about 37° C. for 3 days were suspended in 1 ml of phosphate buffer. The aliquots (0.1 ml) thereof were spread on various media, which was followed by culture under microaerobic conditions at 37° C. for 4–6 days, and the colonies grown were counted. The results of three repeats of these procedures are shown in the following in mean±SE of viable counts (log CFU/ml).

The viable counts on HPSMY medium which is one of the isolation media of the present invention was greater than those on a commercially available selective medium, modified Skirrow medium (manufactured by Nissui Seiyaku) and almost comparable to those on a non-selective medium, GC medium (manufactured by Difco).

| Medium | Viable counts (log CFU/ml) |
|---|---|
| selective medium HPSMY medium (medium of invention) | 8.61 ± 0.12 |
| selective medium modified Skirrow medium (manufactured by Nissui Seiyaku) | 7.76 ± 0.17 |
| non-selective medium GC medium (Difco) | 9.00 ± 0.8 |

EXPERIMENTAL EXAMPLE 4

In the same manner as in Example 1, *Helicobacter pylori* ATCC 43504 broth culture ($2.5 \times 10^8$ CFU) was orally inoculated to prepare infected Mongolian gerbils. Using these infected Mongolian gerbils, the eradication effect of an anti-*Helicobacter pylori* active substance was examined in the same manner as in Example 3.

To be specific, amoxicillin (AMPC, 1 or 3 mg/kg) was orally administered to five Mongolian gerbils at 4 weeks postinfection twice a day for 5 days. At 4 weeks after the final administration of the drug, the stomachs were aseptically excised, placed in phosphate buffer—physiological saline (10 ml) after softly removing their contents, and homogenized with a glass homogenizer. The supernatant was appropriately diluted and an aliquot (0.1 ml) thereof was inoculated onto the isolation medium of Example 2. The medium was cultured for 5 or 6 days in a $CO_2$ incubator and dark brown swelling colonies characteristic of *Helicobacter pylori* were counted. Based on the results, intragastric viable counts are calculated in the same manner as in Example 3.

The viable counts (log CFU) of the group administered with amoxicillin (3 mg/kg) were 3.59±0.82, and significantly smaller than those (5.17±0.27) of the group without administration, thus demonstrating evident eradication effect. However, the viable counts of the group administered with 1 mg/kg of the drug were 5.39±0.16 and eradication effect was not observed.

EXPERIMENTAL EXAMPLE 5

In the same manner as in Example 1, *Helicobacter pylori* ATCC 43504 broth culture ($2 \times 10^8$ CFU) is orally administered to prepare infected Mongolian gerbils. At 4 weeks after the infection, a test compound, 2-((3-methyl-4-(2-(2-methoxyethoxy)ethylthio)-2-pyridyl)-methylthio)-1H-benzimidazole hydrochloride (compound of Example 17 of WO 95/11897, 10 mg/kg) is orally administered to five Mongolian gerbils three times a day for 14 days.

At 4 weeks after the final administration of the drug, the stomachs are aseptically excised, placed in phosphate buffer—physiological saline (10 ml) after softly removing their contents, and homogenized with a glass homogenizer, in the same manner as in Example 1. The supernatant is appropriately diluted and an aliquot (0.1 ml) thereof is inoculated onto the isolation medium of Example 2. The medium is cultured for 5 or 6 days in a $CO_2$ incubator and dark brown swelling colonies characteristic of *Helicobacter pylori* are counted. Based on the results, intragastric viable counts are calculated in the same manner as in Example 3.

The viable counts (log CFU) of the group without administration of the test compound were 5.00±0.20, while those of the group administered with the test compound were 2.81±0.44 (significant difference by $p<0.01$ from the group without administration by Tukey's detection), thus demonstrating evident eradication effect.

EXPERIMENTAL EXAMPLE 6

In the same manner as in Example 1, *Helicobacter pylori* ATCC 43504 broth culture ($1.8 \times 10^8$ CFU) is orally administered to prepare infected Mongolian gerbils. At 4 weeks postinfection, a quinolone synthetic antibacterial agent, levofloxacin (LVFX) 10 mg/kg, is orally administered twice a day for 5 days.

At 3 days after the final administration, the stomachs are aseptically excised, placed in phosphate buffer—physiological saline (10 ml) after softly removing their contents, and homogenized with a glass homogenizer, in the same manner as in Example 1. The supernatant is appropriately diluted and an aliquot (0.1 ml) thereof is inoculated onto the isolation medium of Example 2. The medium is cultured for 5 or 6 days in a $CO_2$ incubator and dark brown swelling colonies characteristic of *Helicobacter pylori* are counted. Based on the results, intragastric viable counts are calculated in the same manner as in Example 3.

The viable counts (log CFU) of the group without administration of the synthetic antibacterial agent were 4.96±0.27, while those of the group administered with levofloxacin (10 mg/kg) were 3.90±1.32 (significant difference by $p<0.01$ from the group without administration by Tukey's detection), thus demonstrating evident eradication effect.

The *Helicobacter pylori*-colonized Mongolian gerbils of the present invention permit nearly 100% intragastric colonization of *Helicobacter pylori*. Inflammatory symptoms caused by *Helicobacter pylori* are observed 2–3 weeks postinfection at superficial gastric mucosa, and the severity of inflammation grows with time. From around 6 months postinfection, gastric ulcer is observed. The Mongolian gerbils of the present invention are useful for screening the therapeutic efficacies of drugs against *Helicobacter pylori*, as well as elucidation of pathology of *Helicobacter pylori* disease in humans.

According to the method of the present invention for preparing *Helicobacter pylori*-colonized Mongolian gerbils, the *Helicobacter pylori*-colonized Mongolian gerbils of the present invention can be prepared with ease, thereby enabling screening of drug which requires a large number of models.

Moreover, the medium of the present invention for isolating *Helicobacter pylori* inhibits growth of bacteria and fungi other than *Helicobacter pylori*, and barely affects growth of *Helicobacter pylori*. Consequently, Helicobacter pylori colonized in Mongolian gerbils which have microorganisms living in stomach can be detected selectively and efficiently.

Since the method of the present invention for screening an anti-*Helicobacter pylori* substance comprises a combined use of the above-mentioned mongolian gerbil models and the medium for isolating *Helicobacter pylori*, the screening of the anti-*Helicobacter pylori* substance can be performed at an animal level, thereby enabling accurate prediction of clinical effects of the anti-*Helicobacter pylori* substance.

What is claimed is:

1. A method of making a gerbil with a gastric ulcer comprising:

(a) obtaining a Mongolian gerbil of an inbred line which is deprived of food for 16–24 hours prior to administration of *H. pylori*, (b) administering a sufficient amount of *H. pylori* to the gerbil of (a) such that gastric ulcers develop using an oral probe, said *H. pylori* being prepared by the method comprising:

(i) culturing *H. pylori* in a selective liquid nutrient medium under microaerobic conditions for 24 hours such that *H. pylori* is selected wherein said liquid medium is selected from the group consisting of GC medium, Brucella medium and brain heart infusion medium, further wherein said liquid medium is supplemented with inactivated horse serum;

(c) depriving the gerbil of (b) of food and water for more than three hours after administration of *H. pylori*;

(d) maintaining the gerbil of (c) for at least 6 months wherein the *H. pylori* colonizes and forms a gastric ulcer.

2. A gerbil which has a gastric ulcer made by the method of claim 1.

3. A method of identifying a compound which is active against *H. pylori* comprising:

(a) administering an effective amount of the test compound to a gerbil with a gastric ulcer of claim 2 for a period effective for decreasing the number of *H. pylori*;

(b) detecting the number of *H. pylori* or *H. pylori* colonies in the stomach of the gerbil of (a), wherein a decrease in the number of *H. pylori* or *H. pylori* colonies indicates an active compound against *H. pylori*.

* * * * *

UNITED STATES PATENT AND TRADEMARK OFFICE
CERTIFICATE OF CORRECTION

PATENT NO.    : 5,929,299
DATED         : July 27, 1999
INVENTOR(S)   : Ikeda et al.

It is certified that error appears in the above-identified patent and that said Letters Patent is hereby corrected as shown below:

<u>Column 10,</u>
Kindly rewrite claims 1-3 as follows:

1. A method of making a gerbil with a gastric ulcer comprising:
    (a) obtaining a Mongolian gerbil of an inbred line which is deprived of food for 16-24 hours prior to administration of *H. pylori*,
    (b) administering a sufficient amount of *H. pylori* to the gerbil of (a) using an oral probe such that gastric ulcers develop, said *H. pylori* being prepared by the method comprising:
        (i) culturing *H. pylori* in a selective liquid nutrient medium selected from the group consisting of GC medium, Brucella medium and brain heart infusion medium, under microaerobic conditions for about 24 hours such that *H. pylori* is selected, said liquid medium being further supplemented with inactivated horse serum;
    (c) depriving the gerbil of (b) of food and water for more than three hours after administration of *H. pylori* ;
    (d) maintaining the gerbil of (c) for at least 6 months allowing for the colonization of *H. pylori* and formation of a gastric ulcer.

2. A gerbil which has a gastric ulcer made by the method of any one of claims 1 and 4-8.

3. A method of identifying a compound which is active against *H. pylori* comprising:
    (a) administering an effective amount of the test compound to the gerbil of claim 2 for a period effective for decreasing the number of *H. pylori*;
    (b) detecting the number of *H. pylori* or *H. pylori* colonies in the stomach of the gerbil of (a), wherein a decrease in the number of *H. pylori* or *H. pylori* colonies indicates an active compound against *H. pylori*.

UNITED STATES PATENT AND TRADEMARK OFFICE
CERTIFICATE OF CORRECTION

PATENT NO. : 5,929,299
DATED : July 27, 1999
INVENTOR(S) : Ikeda et al.

It is certified that error appears in the above-identified patent and that said Letters Patent is hereby corrected as shown below:

Kindly add the following new claims:

-- 4. The method of claim 1, wherein said *H. pylori* develops a gastric ulcer in humans.

5. The method of claim 1, wherein said *H. pylori* is strain ATCC 43504 or strain ATCC 43526.

6. The method of claim 1, wherein said gastric ulcer is similar to a human gastric ulcer in location and pathohistology.

7. The method of claim 1, wherein said gerbil is of an inbred line, MGS/Sea.

8. The method of claim 1, wherein said gerbil is colonized with $10^4$ to $10^5$ colony forming units of *H. pylori*.

9. The method of claim 3, wherein step (b) comprises:
　(i) preparing a homogenate supernatant of the stomach of the gerbil of step (a),
　(ii) culturing an aliquot of the homogenate supernatant on a nutrient medium selected from the group consisting of GC medium, Brucella medium or brain heart infusion, said nutrient medium being further supplemented with defibrinated horse blood, vancomycin, trimethoprim, amphotericin B, polymyxin B and 2,3,5-triphenyltetrazolium chloride to isolate and culture *H. pylori* colonies, and
　(iii) comparing the number of colonies obtained using the test compound with the number of colonies obtained by culturing the homogenate supernatant of the stomach of the gerbil without administration of the test compound wherein a decrease in a number of *H. pylori* or *H. pylori* colonies indicates an active compound against *H. pylori*. --

UNITED STATES PATENT AND TRADEMARK OFFICE
CERTIFICATE OF CORRECTION

PATENT NO. : 5,929,299
DATED : July 27, 1999
INVENTOR(S) : Ikeda et al.

It is certified that error appears in the above-identified patent and that said Letters Patent is hereby corrected as shown below:

Please rewrite the title as follows:
-- *HELICOBACTER PYLORI*-COLONIZED MONGOLIAN GERBILS, METHOD FOR PREPARATION THEREOF, MEDIUM FOR ISOLATING *HELICOBACTER PYLORI*, AND METHOD FOR SCREENING ANTI-*HELICOBACTER PYLORI* SUBSTANCE USING THEM --

Signed and Sealed this

Fifth Day of March, 2002

Attest:

JAMES E. ROGAN
*Attesting Officer*     *Director of the United States Patent and Trademark Office*